United States Patent [19]
Driver et al.

[11] Patent Number: 5,640,804
[45] Date of Patent: Jun. 24, 1997

US005640804A

[54] PEST TRAP PLANTS AND CROP PROTECTION

[75] Inventors: John Driver, Modesto; Abhaya M. Dandekar, Davis, both of Calif.

[73] Assignees: The Regents of the University of California, Oakland; Treetech Management Inc., DBA Dry Creek Laboratories, Modesto, both of Calif.

[21] Appl. No.: 309,233

[22] Filed: Sep. 14, 1994

[51] Int. Cl.$^6$ .................. A01G 1/00; A01G 13/10; C12N 15/82; C12N 15/32; A01H 5/00

[52] U.S. Cl. .............. 47/58; 800/205; 800/DIG. 31; 800/DIG. 35; 800/DIG. 66; 435/69.1; 435/69.2; 435/70.1; 435/172.3; 536/23.6; 536/23.71

[58] Field of Search .................. 435/69.1, 70.1, 435/172.3, 69.2; 47/58; 536/23.71, 23.6; 800/205, DIG. 31, DIG. 35, DIG. 66

[56] References Cited

U.S. PATENT DOCUMENTS 5,229,112  7/1993  Obukowicz ............... 424/93.2

OTHER PUBLICATIONS

Cantelo, W.W., et al. (1984) "Insect Population Response to Mixed and Uniform Plantings of Resistant and Susceptible Plant Material", *Environmental Entomology*, 13(5):1443–1445.

Cantelo, W.W., et al. (Mar. 1994) "The Use of Transgenic Potatoes in Simulated Trap Cropping Systems", (Computer Abstract) Agricultural Research Service. Michigan State University, East Lansing, MI.

Dandekar et al. 1994. Plant Science 96(1–2): 151–162.

Dandekar et al. 1992. Brighton Crop Prot. Conf. vol. 2, No. 7B–2: 741–747.

James et al. 1989. Plant Cell Reports 7:658–661.

Gay et al. 1973. Plant Disease Reporter 57(8): 684–688.

Hilder et al. 1987. Native 300: 160–163.

*Primary Examiner*—David T. Fox
*Attorney, Agent, or Firm*—Townsend and Townsend and Crew LLP

[57] ABSTRACT

The present invention provides new methods for controlling plant pests using transgenic plants. The methods control pests on a desired crop plant using transgenic pest trap plants of a different species or variety which are preferred host for the target pest, and thereby preferentially attract the pest. The pest trap plants comprise a gene encoding a protein toxic to the pest.

16 Claims, No Drawings

PEST TRAP PLANTS AND CROP PROTECTION

BACKGROUND OF THE INVENTION

The present invention relates to the field of recombinant DNA technology. In particular, it relates to methods for using genes encoding pesticidal proteins to control pests on agronomic important plants.

Synthetic chemicals are relied on extensively for protection against a wide variety of pests in the agriculture and forestry industries. The use of chemical pesticides, however, have posed several problems. In particular, many insect pests have developed resistance to widely used compounds. In addition, widespread use has led to concerns about environmental pollution. Many of these compounds have deleterious effects on non-target organisms, such as birds, and humans. The compounds may also accumulate in the food chain and affect natural predators of insect pests.

These concerns have led to increased emphasis on alternative pest management strategies. For instance, genes from viruses and bacteria that encode proteins that are toxic to insects and other pests have been used to control pests. The most commonly used of these proteins is a toxin protein from a gram-positive soil bacterium, *Bacillus thuringiensis* (Bt toxin). *B. thuringiensis* produces a proteinaceous paraspore or crystal which is toxic upon ingestion by a susceptible insect host. The cloning and expression of Bt toxin genes has been described in the literature (Schnepf, H. E. and Whitely, H. R. *Proc. Natl. Acad. Sci. USA* 78: 2893–2897 (1981)). U.S. Pat. Nos. 5,236,843, 5,26,166, and 5,135,867. Transgenic plants expressing this protein have been used to control a variety of plant pests.

The use of transgenic plants in food crops raise other problems, however. For instance, public resistance and added regulatory burdens hinder the production and sale of transgenic food crop plants. In addition, in the case of perennial crops, the cost of replacing orchards, vineyards and the like with transgenic cultivars may be prohibitive.

Thus, a need exists for new approaches to apply the advances in plant genetic engineering to control pests. The present invention addresses these and other needs.

SUMMARY OF THE INVENTION

The present invention provides methods of controlling pests on a first plant. The methods comprise planting a second plant adjacent the first plant, wherein the second plant is preferred host for the pest and comprises a heterologous pesticidal gene. The second plant is referred to here as a pest trap plant.

The pest is preferably an insect or nematode pest. An exemplary insect pest is the codling moth. Typically, the heterologous pesticidal gene encodes *Bacillus thuringiensis* toxin effective against lepidopteran insect pests. Another example of a heterologous pesticidal gene is one that encodes cowpea trypsin inhibitor.

Typically, the second plant is a member of species different from that of the first plant. In some embodiments, the second plant is an uncultivated plant. An exemplary pest trap plant is apple to be used in combination with either walnut or pear. The pest trap plant may be planted in the same field as the first plant.

Also claimed are fields comprising a crop plant of interest and a pest trap plant. The pest trap plant is a preferred host for a plant pest of the crop plant of interest and comprises a heterologous pesticidal gene.

The invention further provides methods of making a pest trap plant for controlling a pest on a desired plant. The methods comprise introducing a pesticidal gene into an uncultivated plant which is a preferred host for the pest. The pesticidal gene may be one that encodes a *Bacillus thuringiensis* toxin. The gene can be introduced using, for example, Agrobacterium. The invention is also directed to transgenic uncultivated plant comprising a heterologous pesticidal gene, which plant is a preferred host for a pest of desired cultivated plant.

Definitions

A "pesticidal gene" is a polynucleotide that, when expressed in a plant cell, prevents infection of the plant by the plant pest. The gene preferably encodes a protein that directly inhibits development of the plant pest and/or is toxic to the pest. An exemplary pesticidal gene of the invention is Bt toxin gene.

A "plant pest" is an organism that deleteriously interferes with normal plant development. A plant pest may attack any plant organ, including leaves, roots, flowers, fruit and the like. Plant pests particularly targeted by the methods of the present invention are those showing behavioral characteristics by which the pest prefers one plant host to another. Such plant pests include insects, nematodes, and the like.

As used herein a plant that is a "preferred host" for a particular plant pest is one that preferentially attracts the pest as compared to a crop plant of interest. The preferred host may be a different cultivar of the same species as the crop plant or may be a different species. The preferred host may be a crop plant or may be a wild or uncultivated species. The reason for the preferential attractiveness of the preferred host is not critical and can be for any reason, e.g., timing of the production of leaves or flowers of the preferred host, or relative lack of inhibitory compounds in leaves or other tissues. The preference of a pest for a particular host plant may be the result of evolutionary relationships between the two organisms, such as the presence of specific chemoattractants in the host plant.

In addition, the degree to which the pest prefers the preferred host over the crop plant of interest is not critical. Typically, however, the methods of the invention are more effective, the greater the difference in preference between the two plants.

A "pest-trap plant" is a preferred host plant that contains the genetic information for a pesticidal gene.

An "uncultivated plant" is a plant that is not a horticulturally or agriculturally derived plant variety typically cultivated in the area of use. Usually, an uncultivated plant is wild species that may or may not be related to the crop plant of interest. For instance, California black walnut may be used as preferred host with English walnut cultivars.

The term "adjacent" as used herein refers to spacing between a pest trap plant and a crop plant. The precise distance between the two plants is not critical to the invention and will depend, among other things, on the crop plant of interest, the pest to be controlled, soil characteristics, and climate conditions in which the plants are used. The two plants are considered adjacent to each other if the pest trap plant is close enough to the crop plant to substantially decrease the pest population on the crop plant. In some cases the pest trap plant is planted within the field or orchard in which the crop plant is grown. Alternatively, the pest trap plant may be planted outside the field to provide a barrier against pest attack.

The term "expression" refers to the transcription and translation of a structural gene so that a protein is synthesized.

The term "operably linked" refers to functional linkage between a promoter and a second sequence, wherein the promoter sequence initiates transcription of RNA corresponding to the second sequence.

The term "plant" includes whole plants, plant organs (e.g., leaves, stems, roots, etc.), seeds and plant cells. The class of plants which can be used in the method of the invention is generally as broad as the class of higher plants amenable to transformation techniques, including both monocotyledonous and dicotyledonous plants. It includes plants of a variety of ploidy levels, including polyploid, diploid and haploid.

The term "promoter" refers to a region of DNA upstream from the structural gene and involved in recognition and binding RNA polymerase and other proteins to initiate transcription. A "plant promoter" is a promoter capable of initiating transcription in plant cells.

DESCRIPTION OF THE PREFERRED EMBODIMENT

The present invention provides new methods for controlling a variety of plant pests using transgenic plants. The methods control pests on a desired crop plant using transgenic pest trap plants of a different species or variety which are the preferred host for the target pest, and thereby preferentially attract the pest. The pest trap plants contain the genetic information encoding a protein toxic to the pest, which results in reduction of the pest population on the desired crop plant.

The methods of the present invention can be used to control any number of plant pests, in particular, insects and nematodes. Any pest against which toxic genes are known, or are later found, may be targeted with the methods of the invention. Typically, insect pests are targeted. A number of insect pests of crop plants have been identified and characterized. For instance, insect pests in the orders Lepidoptera (butterflies, moths), Coleoptera (beetles), Diptera (flies, mosquitoes), and Orthoptera (locusts, grasshoppers, crickets) have been extensively studied. Exemplary insect pests include codling moth, walnut husk fly, apple maggot, medfly, navel orange worm, leaf rollers, oriental fruit moth, colorado potato beetle, sweet potato white fly, lygus bugs, leaf hoppers, aphid, spider mites.

In addition, various nematode species can be controlled using the methods of the invention. Especially significant in terms of crop losses are the sedentary endoparasites, cyst nematodes (Globodera spp. and Heterodera spp.) and root-knot nematodes (Meloidogyne spp.). Root-knot nematodes affect over 2,000 species of plants, including most of the major crops in the world.

The invention can also be used for control of insects which serve as vectors for plant pathogens such as viruses, fungi, bacteria and other microorganisms. Examples include the leaf hopper, which is a vector for mycoplasma infection in cherries, psylla spreads a mycoplasma that destroys pear trees. Other examples are sweet potato white fly which spreads a virus that causes infectious yellows of chole crops.

Construction of Expression Vectors

The methods required for the recombinant expression of desired genes in transgenic plants are well known to those of skill in the art. Briefly, expression cassettes comprising an appropriate promoter is operably linked to a structural gene encoding a desired protein is introduced into the plant. Construction of appropriate expression vectors is carried out using standard techniques.

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989).

The minimal requirements of the vector are that the desired nucleic acid sequence be introduced in a relatively intact state. Thus, any vector which will produce a plant carrying the introduced DNA sequence should be sufficient. The selection of vectors and methods to construct them are commonly known to persons of ordinary skill in the art and are described in general technical references (See, in general, *Methods in Enzymology* Vol. 153 ("Recombinant DNA Part D") 1987, Wu and Grossman Eds., Academic Press.

The recombinant vectors of the present invention typically comprise an expression cassette including a promoter for initiating transcription of the desired polynucleotide sequences in plants. Companion sequences, of bacterial origin, are also included to allow the vector to be cloned in a bacterial host. The vector will preferably contain a broad host range prokaryote origin of replication. A selectable marker should also be included to allow selection of bacterial cells bearing the desired construct. Suitable prokaryotic selectable markers include resistance to antibiotics such as kanamycin, gentamycin or tetracycline.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

The promoter may be "constitutive" and direct expression of the gene in all tissues of a regenerated plant. Such promoters are typically active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumafaciens=1*, and other transcription initiation regions from various plant genes known to those of skill.

Alternatively, the plant promoter may direct expression of the gene in a specific tissue or may be otherwise under more precise environmental or developmental control. Such promoters are referred to here as "inducible" promoters. Examples of environmental conditions that may effect transcription by inducible promoters include anaerobic conditions or the presence of light.

Examples of promoters under developmental control include promoters that initiate transcription only in certain tissues, such as roots, fruit, seeds, or flowers. Using a particular organ-specific promoter expression of the genes can be targeted to desired tissues within the plant. For instance, a fruit specific promoter can be used to target expression of toxin genes to flowers, fruit or seed to target pests that attack these tissues. For a general description of suitable promoters, see, Okamuro, J. K. and Goldberg, R. B. *Regulation of plant gene expression: general principles in The Biochemistry of Plants: A Comprehensive Treatise* Vol. 15 (1989)).

For control of nematodes, a root specific promoter is particularly useful for controlling nematodes. Alternatively, the use of promoters from nematode induced genes, such as ToRb7, may be used (See, e.g., International Publication No. WO 93/06710). These promoters can be used to drive expression of genes toxic to plant cells and thus deprive the sedentary nematode of a food source. Alternatively, the structural gene may be toxic to the nematode itself.

For expression of polypeptides in plants, the recombinant expression cassette will contain, in addition to the desired polynucleotide sequence and the promoter, a transcription initiation site (if the sequence to be transcribed lacks one), and a transcription termination sequence. The termination region may be obtained from the same gene as the promoter sequence or may be obtained from different genes.

If the mRNA encoded by the structural gene is to be efficiently translated, polyadenylation sequences are also commonly added to the vector construct. Alber and Kawasaki, *Mol. and Appl. Genet*, 1: 419–434, 1982. Polyadenylation sequences include, but are not limited to the Agrobacterium octopine synthase signal (Gielen et al., *EMBO J.*, 3: 835–846, 1984) or the nopaline synthase signal (Depicker et al., *Mol. and Appl. Genet*, 1: 561–573, 1982).

The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow in a medium containing the particular antibiotic. Additionally the vectors may also contain a scorable marker gene encoding the enzyme β-glucuronidase (GUS) that can be visually detected in transgenic tissue and aids in screening plant transformants.

The particular pesticidal structural gene used to inhibit plant pests is not a critical aspect of the invention. A variety of such genes are known in the art. The most widely used microbial toxin genes are derived from the bacterium *Bacillus thuringiensis*. The cloning and expression of this Bt toxin many genes has been described. The toxin genes from different *B. thuringiensis* strains are effective against different insects. Bt toxins active against members of lepidoptera (moths and butterflies), Diptera (flies and mosquitos) and coleoptera (beetles) have been described. U.S. Pat. Nos. 5,236,843, and 5,135,867 describe toxin genes effective against lepidopteran species. A gene encoding a nematode-active toxin is described in U.S. Pat. No. 5,236,843.

Other insecticidal and nematicidal genes include those encoding proteinase inhibitors such as cowpea trypsin inhibitor (described in WO 92/15690), soybean lipoxidase, polyphenol oxidase, wheat α-amylase, snow drop lectin and a variety of different plant lectins. For a description of suitable genes see, Hilder, V. A. et al. *Genes for protecting transgenic crops from chewing and sap-sucking insect pests in Proceedings of the Brighton Crop Protection Conference on Pests and Diseases* Vol. 2: 731–740 (1992)).

B. Plant Transformation

The various DNA constructs described above may be introduced into the genome of the desired plant by a variety of conventional techniques. For example, the DNA construct may be introduced directly into the genomic DNA of the plant cell using polyethylene glycol precipitation (Paszkowski et al. *Embo J.* 3: 2717–2722 (1984)) electroporation and microinjection of plant cell protoplasts (Fromm et al. *Proc. Natl. Acad. Sci. USA* 82: 5824 (1985)), or the DNA constructs can be introduced into plant tissue using ballistic methods, such as DNA particle bombardment (Klein et al. *Nature* 327: 70–73 (1987)). Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker gene(s) into the plant cell DNA when the cell is infected by the bacteria. For a review of gene transfer methods for plant and cell cultures see, FisK, H. J. and Dandekar, A. M. *The introduction and expression of transgenes in crop plants in Scientia Horticulturae* 55: 5–36 (1993) and Potrykus *CIBA Found. Symp.* 154: 198 (1990).

*Agrobacterium tumefaciens*-meditated transformation techniques are the most commonly used techniques for transferring genes into plants. These techniques are well described in the scientific literature. See, for example Horsch et al. *Science* 233: 496–498 (1984), Fraley et al. *Proc. Natl. Acad. Sci. USA* 80: 4803 (1983), and Hooykaas *Plant Mol. Biol.* 13: 327–336 (1989).

All species which are a natural plant host for Agrobacterium are transformable in vitro. Most dicotyledonous species can be transformed by Agrobacterium. Monocotyledonous plants, and in particular, cereals, are not natural hosts to Agrobacterium. There is growing evidence now that certain monocots can be transformed by Agrobacterium. Using novel experimental approaches cereal species such as rye (de la Pena et al., *Nature* 325: 274–276, 1987), corn (Rhodes et al., *Science* 240: 204–207, 1988), and rice (Shimamoto et al., *Nature* 338: 274–276, 1989) may now be transformed.

Transformation of a number of woody plants using Agrobacterium and other methods has been described. (Shuerman, P. L. and Dandekar, A. M. *Transformation of Temperature Crop Species: Progress and Potentials in Scientia Horticulturae* 55: 101–124 (1993)). For instance, regeneration and transformation of apples is described in James et al. *Plant Cell Rep.* 7: 658–661 (1989). Tissue culture procedures for apple including micropropagation, (Jones, O. P. *Nature* 262: 392–393 (1976); Zimmerman, R. H. *In Methods in Fruit Breeding*, pp. 124–135 (1983)) and adventitious bud formation (James, D. J. *Biotechnology and Genetic Engineering Reviews*, vol. 5: 33–79 (1987)) have also been described.

After transformation, transformed plant cells or plants comprising the introduced DNA must be identified. A selectable and/or scorable marker genes such as those discussed above is typically used. Transformed plant cells can be selected by growing the cells on growth medium containing the appropriate antibiotic. In some instances, the presence of opines can also be used if the plants are transformed with Agrobacterium.

After selecting the transformed cells, one can confirm expression of the introduced structural genes. Simple detection of mRNA encoded by the inserted DNA can be achieved by well known methods in the art, such as Northern blot hybridization. The inserted sequence can be identified using the polymerase chain reaction (PCR) and Southern blot hybridization, as well. See, e.g., Sambrook, supra.

Transformed plant cells (e.g., protoplasts) which are derived by any of the above transformation techniques can be cultured to regenerate a whole plant which possesses the transformed genotype and thus the desired pest resistant phenotype. Such regeneration techniques rely on manipulation of certain phytohormones in a tissue culture growth medium. Plant regeneration from cultured protoplasts is described in Evans et al., *Protoplasts Isolation and Culture*,

*Handbook of Plant Cell Culture*, pp. 124–176, MacMillan Publishing Company, New York, 1983; and Binding, *Regeneration of Plants, Plant Protoplasts*, pp. 21–73; CRC Press, Boca Raton, 1985. Regeneration can also be obtained from plant callus, explants, organs, or parts thereof. Such regeneration techniques are described generally in Klee et al. *Ann. Rev. of Plant Phys.* 38: 467–486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Pest Trap Plants

The invention has use in producing pest trap cultivars of any plant susceptible to infection by the target pests. Any plant can be used in the invention so long as it is a preferred host for the target pest and is capable of being transformed and regenerated. The basis for the pest trap plant being a preferred host for the pest is not critical to the invention. For instance, the plant may be a different cultivar of the same species as the plant for which pest protection is sought. If the first cultivar produces flowers or leaves when the pests are most prevalent, it will preferentially attract and eliminate the target pest.

Typically, the pest-trap plant will be a different species than that of the crop plant. The host preferences of many pests are known and well documented in the literature. For a discussion of host pest interactions see, Bernays, E. A. and Chapman, R. F. *Host-Plant Selection by Phytophagous Insects* (1994).

Preferred hosts for particular pests are well described in the literature. Typically, such plants are identified as plants to be cleared from areas in which the particular crop plant is being grown. For instance, it is generally recommended that because black walnut trees are favorite host of Walnut Husk Fly, these trees be removed from orchards of English walnuts. *Integrated Pest Management for Walnuts*, 2nd Ed., University of California, Statewide Integrated Pest Management Project, Publication 3270, pg. 45. In addition, it is generally recommended that lygus bug hosts (e.g., wild radish and vetch) be removed from peach, plum and nectarine orchards to reduce breeding populations. *Peaches, Plums and Nectarine Growing and Handling for Fresh Market*, University of California Cooperative Extension, Division of Agriculture and Natural Resources, Publication 3270. The rosy apple aphid spends part of its life cycle on an alternate host, the most common is buckhorn plantain, *Plantago lanceolata*, known also as ribgrass. It is recommended that plantain growing in and near the orchard be removed to eliminate the summer host of this pest. *Integrated Pest Management for Apples and Pears*, University of California, Statewide Integrated Pest Management Project, Publication 3340; pg. 124–126.

Other examples of combinations of species include the use of apple as a preferred host to walnut or pear for codling moth; hawthorn as a preferred host to apple for apple maggot; quince as preferred host for Oriental Fruit Moth; alfalfa, wild radish, vetch as preferred hosts for lygus bugs; buffalobar (*Soanum rostratum*), black nightshade, cutleaf nightshade, groundcherries as preferred hosts for Colorado Potato Beetle; and Mock Orange as preferred host for Mediterranean Fruit Fly.

The pest-trap plant may also be bred or genetically engineered to increase its attractiveness to the target pest. For instance, increasing levels of phagostimulants which are nutrients, especially sugars can be used to increase attractiveness.

The invention thus has use over a broad range of cultivated plants, including species from the genera Trifolium, Medicago, Phaseolus, Pisum, Vigna, Glycine, Citrus, Linum, Geranium, Manihot, Daucus, Arabidopsis, Brassica, Raphanus, Capsicum, Datura, Hyoscyamus, Lycopersicon, Nicotiana, Solanum, Petunia, Digitalis, Cichorium, Helianthus, Chrysanthemum, Vitus, Lactuca, Asparagus, Cucumis, Cucurbita, Malus, Pyrus, Prunus, Rosa, Fragaria, Tarro, Ananas, Musa, Cacoa, Beta, Coffea, Gossypium, Thea, Dioscorea, Arachis, Citrullus, Juglans, Olea, Cannabis, Triticum, Hordeum, Avena, Festuca, Sorghum, Oryza, Secale, and Zea.

In addition a number of uncultivated species can be used in the invention. Examples include hawthorn, California black walnut, privet, buckhorn plantain, wild radish, vetch, buffalobar, black nightshade, cutleaf nightshade, groundcherries, wild mustard, wild blackberries, and the like.

The following examples illustrate, but do not limit, the invention.

EXAMPLE 1

This example describes the production of transgenic apple plants expressing Bt toxin particularly effective against Lepidopteran species. These transgenic plants are useful in the control of codling moth on walnuts.

Vectors for Introduction and Expression of Insect Pest Tolerance in Apple Trees

Two vectors provided by Calgene (Davis, CA) were modified by introducing a gene encoding GUS (β-glucuronidase). The constructs contain a chemically synthesized truncated cry1Ac gene. In one of the vectors the chemically synthesized truncated gene was further modified (by Calgene) with the addition of the 5'-noncoding sequences to further improve the translational efficiency of this gene thus further improving its expression.

The vectors were further modified by introducing the gene encoding GUS thus creating two new vectors pDU92.67 and pDU92.63 containing both possible orientations of GUS and the modified cry1Ac gene. In a similar manner the vector comprising the gene without the 5' modification was modified creating pDU92.710 and pDU92.15. These binary vectors were then introduced into three different strains of Agrobacterium, C58C1, EHA101 and AGL1 to create a functional delivery system.

Apple Transformation Procedure

Apples were transformed using the methods described in James, D. J. and Dandekar, A. M. *Regeneration and transformation of apple (Malus pumila Mill.) in Plant tissue culture manual: Fundamentals and applications*, B8: 1–18 (1991).

Analysis of Transgenic Apple Plants

After regeneration and selection, putative transgenic shoots representing independent transformation events were multiplied through micropropagation (shoot cultures). For each construct used several transformations were performed to obtain enough independent transformation events (10–20). Northern analysis of the construct and quantitation of GUS activity were used to analyze the level of expression in each of the transformants. We have found that the level of GUS is a good indicator of plant cell transformation.

The independent transformation events were initially confirmed by PCR analysis. DNA was extracted from individual transformed apple shoot lines and primers specific for GUS and APH marker genes and the Bt gene were used. PCR products were confirmed by diagnostic restriction endonuclease cleavage and Southern hybridization with the corresponding gene sequences according to standard techniques.

Transformation events were eventually verified using Southern blot hybridization. This analysis involves the identification of internal T-DNA fragments and the determination of copy number of inserts through hybridization of right border regions as previously described. Both right border and internal fragment probes were used as described before (Dandekar et al., *Agrobacterium-mediated transformation of somatic embryos as a method for the production of transgenic plants* in *J. Tissue Cult. Meth.* 12: 145–150 (1989), McGranahan et al. *Improved efficiency of the walnut somatic embryo gene transfer system* in *Plant Cell Rep.* 8: 512–516 (1990) to distinguish independent transformation events and to determine the copy number of the inserted DNA. Transgenic plants containing single copies as well as those representing independent transformation were then used for further experiments.

Efficacy Testing for Pest Resistance

The insect pathology and bioassays are then conducted to determine resistance against the target insect species codling moth (CM). The susceptibility of CM to the purified preparations of the insecticidal crystal proteins (ICPs) of (Bt) have been previously determined by feeding experiments described earlier (Vail et al. *Response of production and postharvest walnut pests to Bacillus thuringiensis insecticidal crystal protein fragments* in *Biological Control* 1: 329–333 (1991).

Qualitative bioassays are first performed on selected tissues obtained to determine mortality and to identify transgenic clones that display mortality that range between 80 to 100%. These will then be further investigated by a quantitative analysis to determine the amount of protein expressed using western blot and specific antibodies directed towards the expressed protein. The transgenic lines that display low or no mortality are discarded based upon the qualitative data.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of controlling an insect pest on a first plant, the method comprising planting a second plant adjacent to the first plant, the second plant being a preferred host for the insect pest and comprising heterologous insecticidal gene.

2. The method of claim 1, wherein the insect pest is codling moth.

3. The method of claim 1, wherein the heterologous insecticidal gene encodes *Bacillus thuringiensis* toxin.

4. The method of claim 3, wherein the *Bacillus thuringiensis* toxin is effective against lepidopteran insect pests.

5. The method of claim 1, wherein the heterologous insecticidal gene encodes cowpea trypsin inhibitor.

6. The method of claim 1, wherein the second plant is a member of species different from that of the first plant.

7. The method of claim 1, wherein the second plant is not an agriculturally derived plant variety.

8. The method of claim 1, wherein the first plant is walnut.

9. The method of claim 1, wherein the first plant is pear.

10. The method of claim 1, wherein the second plant is apple.

11. The method of claim 1, wherein the second plant is planted in the same field as the first plant.

12. A field comprising a crop plant of interest and a insect pest trap plant, the insect pest trap plant being a preferred host for a plant insect pest of the crop plant of interest and comprising a heterologous insecticidal gene.

13. The field of claim 12, wherein the crop plant and insect pest trap plant are members of different species.

14. The field of claim 12, wherein the crop plant is walnut and the insect pest trap plant is apple.

15. The field of claim 12, wherein the crop plant is pear and the insect pest trap plant is apple.

16. The field of claim 12, wherein the insecticidal gene encodes *Bacillus thuringiensis* toxin.

* * * * *